(12) United States Patent
Griffiths et al.

(10) Patent No.: US 7,803,924 B2
(45) Date of Patent: Sep. 28, 2010

(54) HSP60 FROM ARTHROBACTER

(75) Inventors: Steven Gareth Griffiths, New Brunswick (CA); Rachael Jane Ritchie, New Brunswick (CA); Nathalie C. Simard, New Brunswick (CA)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/924,986

(22) Filed: Oct. 26, 2007

(65) Prior Publication Data

US 2008/0287664 A1  Nov. 20, 2008

Related U.S. Application Data

(62) Division of application No. 10/543,366, filed as application No. PCT/EP2004/001368 on Feb. 13, 2004, now Pat. No. 7,297,783.

(30) Foreign Application Priority Data

Feb. 14, 2003  (GB) .................... 0303507

(51) Int. Cl.
*C07H 21/04* (2006.01)
(52) U.S. Cl. .................... 536/23.4
(58) Field of Classification Search ........ None
See application file for complete search history.

(56) References Cited

U.S. PATENT DOCUMENTS

| 5,165,925 | A | * | 11/1992 | Leong .................... 424/186.1 |
| 5,858,773 | A | | 1/1999 | Mazodier et al. |
| 6,482,614 | B1 | | 11/2002 | Young |

FOREIGN PATENT DOCUMENTS

| WO | WO 88/05823 | 8/1988 |
| WO | WO-8805823 A2 | 8/1988 |
| WO | WO 99/32634 | 7/1999 |
| WO | WO-9932634 A2 | 7/1999 |
| WO | WO 01/04344 | 1/2001 |
| WO | WO 0104344 A2 * | 1/2001 |
| WO | WO-0104344 A2 | 1/2001 |
| WO | WO 01/16174 | 3/2001 |
| WO | WO 0116174 A2 * | 3/2001 |
| WO | WO-0116174 A2 | 3/2001 |
| WO | WO 2004/007539 | 1/2004 |
| WO | WO-2004007539 A2 | 1/2004 |

OTHER PUBLICATIONS

De Bruyn et al. (Microbiol., 146:1513-1524, 2000).*
Invitrogen Product Catalog, 1997.*
Newport, "Heat Shock Proteins as Vaccine Candidates", Seminars in Immunology, vol. 3, No. 1, pp. 17-24, (1991).
Bowie et al., (Science, 1990, 247:1306-1310).
Burgess et al., (J. of Cell Bio. 111:2129-2138, 1990).
Lazar et al., (Molecular and Cellular Biology, 1988, 8:1247-1252).
Bork (Genome Research, 2000, 10:398-400).
Sigmund, Arterioscler. Thromb. Vasc. Biol., 20:1425-1429, 2000.
Bampton et al., Brain Res., 841:123-134, 1999.
Lodish et al., Mol. Cell Biol., 3rd ed. Scientific American Books, NY, 1995, p. 115.

* cited by examiner

*Primary Examiner*—Robert B Mondesi
*Assistant Examiner*—Brian J Gangle

(57) ABSTRACT

The hsp60 gene from a strain of *Arthrobacter* has been isolated and sequenced. The encoded protein is believed to be highly immunogenic, especially in fish, and also has utility as a non-specific adjuvant, and as an adjuvanting carrier for heterologous antigens.

2 Claims, No Drawings

SEQUENCE LISTING

```
<160> NUMBER OF SEQ ID NOS: 7

<210> SEQ ID NO 1
<211> LENGTH: 2585
<212> TYPE: DNA
<213> ORGANISM: Arthrobacter spp.

<400> SEQUENCE: 1
ggcccggact ggtctgccgg accccgcctc agctttgtgc cgccgggcgt ccggggatca      60
acccaccagc ggaatgcctt tggcatcggt ccggaagttg tccgagccga tcagaatcag     120
gattccttcg atgaatcccc aaatcgcgga gacgaacgac agaaacccga gcgagagcac     180
agtgatcagc aactgggcca cggccttgcc ggtgtaaccc agataaaagt tatgcacgcc     240
gaaagccccg agcagaatgc ccagcagccc ggccagaacc ttgttcttgc ccatggcgcc     300
ggcatacccg ggtgcgtagc cgggctgact gtagttcggc tggttgtagt tctgttggct     360
gtggttctgt ggcggagccg ggtaggccgg tggcgcatca ctggctggag ccggataagc     420
ctggggtgtt ccgaaggccg ccggtgtccc gtatgccgcc ggtgtcccgt acgccgccgg     480
ctcctgccgg gccgtctcgg aatcgggttc cgggatgctt ggcttctcgc tcatgctgat     540
cgctccatct ggtgagggtc gaactgaccg ttcgggcaaa ttcccgatac ggcaggtatc     600
tctcactgaa ggctagccag gcgacattgc gatctccaca gttttggccc tttttggggg     660
gtcaatccgg gaaaccacct agtggttcgg ggagtgcgcc gatttcgcgc tgagcctaag     720
cggccgaatt ccgctgtcct ctgcttgcac tctcacccct cgagtgctaa ttattgagtt     780
agcactctcc tgttatgact gctaagaatt tcgagtcgga caggggattc gaccagatcg     840
gcgaggtgct cggctcgatg taccgaattc atcggccggg ttgccgtccg tcgcgggcgc     900
cgaagtctgg tcatgttcct cacatgattg tcccgaaagg actgaagcct ccatggccaa     960
gatcattgca ttcgatgaag aggcgcgccg cggcctcgag cggggattga acatcctcgc    1020
cgacgccgtc aaggtgaccc tcggcccgcg cggccgcaac gtcgtgctgg aaaagaagtg    1080
gggcgccccc acgatcacca acgatggcgt gtccatcgcc aaggagatcg agctggagga    1140
cccgtacgag aagatcggcg ccgagctggt caaggaagtc gccaagaaga ctgacgaagt    1200
cgccggcgac ggtaccacca ccgctaccgt tttggcccag gccctggttc gcgaaggcct    1260
gcgcaacgtc gcagccggcg ctgatccgct gagcctcaag cgcggcatcg agaaggctgt    1320
cgccgcggtg accgagcagc tgctggcttc cgccaaggaa gtcgagacca aagaagagat    1380
cgcggccact gcttcgatct cggccgcgga cacccagatc ggcgcgttga tcgccgaagc    1440
cctggacaag gtcggcaaag aaggcgtcat cacggtcgaa gagtccaaca ccttcggtct    1500
ggaactcgag ctcaccgaag gcatgcgctt cgacaagggc tacatctcgc agtacttcgt    1560
caccgacgcc gagcgccagg agacggtcct cgaggatccc tacatcctga tcgtcaactc    1620
caagatctcc aatgtcaaag acatggtcgc gatcctggaa aaggtcatgc agtccggcaa    1680
```

```
gcccttgctg atcatcgcgg aagacgtcga agccgaggct ttggcgaccc tcatcgtgaa    1740
caagatccgc gggctattca agtcggttgc ggtcaaggct cccggcttcg gcgaccgccg    1800
caaggcccag ctggccgaca tcgcgatcct caccggcggc caagtcatct cggaagaggt    1860
cggcttgagc ttggaaaacg ccacgctgga cctgttgggc caggcgcgca aggtcgttgt    1920
caccaaggac gagaccacca ttgtggaagg cgctggcgat gccgagcaga ttgcgggccg    1980
agtcgcccag atccgcgccg aaatcgacaa ctccgattcc gattacgacc gtgagaagct    2040
gcaggaacgt ctggccaagc tggccggcgg cgttgccgtg atcaaggccg gtgcggcaac    2100
cgaggtcgag ctcaaagagc gcaagcaccg tatcgaagac gcggtccgca acgccaaggc    2160
tgcagtcgaa gagggcatcg tccccggcgg tggagtggct ttgatccagg ccggcgtcaa    2220
ggcattcgaa accttggacc tcgaaggcga tgaggctact ggcgcgaaca tcgtgcgggt    2280
cgccatcgat gccccgttga agcagatcgc gatcaatgct ggtctggagc cgggcgtcgt    2340
cgtcgacaag gtgcgtggct tgccggtcgg gcacggcctc aacgctgcta ccggagtcta    2400
tgaggatctg ctccccgcag gcgtcaacga tccggtcaag gtgacccgct ctgcactgca    2460
gaacgcggcc tcgattgctg gcttgttcct caccacggaa gttgtggttg cagataagcc    2520
gcagaagaat gttccggcag cgccgggcgg agacgaaatg ggtggcatgg acaactgaaa    2580
gggcg                                                                2585
```

<210> SEQ ID NO 2
<211> LENGTH: 541
<212> TYPE: PRT
<213> ORGANISM: Arthrobacter spp.

<400> SEQUENCE: 2

```
Met Ala Lys Ile Ile Ala Phe Asp Glu Glu Ala Arg Arg Gly Leu Glu
 1               5                  10                  15

Arg Gly Leu Asn Ile Leu Ala Asp Ala Val Lys Val Thr Leu Gly Pro
             20                  25                  30

Arg Gly Arg Asn Val Val Leu Glu Lys Lys Trp Gly Ala Pro Thr Ile
         35                  40                  45

Thr Asn Asp Gly Val Ser Ile Ala Lys Glu Ile Glu Leu Glu Asp Pro
     50                  55                  60

Tyr Glu Lys Ile Gly Ala Glu Leu Val Lys Glu Val Ala Lys Lys Thr
 65                  70                  75                  80

Asp Glu Val Ala Gly Asp Gly Thr Thr Thr Ala Thr Val Leu Ala Gln
                 85                  90                  95

Ala Leu Val Arg Glu Gly Leu Arg Asn Val Ala Gly Ala Asp Pro
             100                 105                 110

Leu Ser Leu Lys Arg Gly Ile Glu Lys Ala Val Ala Val Thr Glu
         115                 120                 125

Gln Leu Leu Ala Ser Ala Lys Glu Val Glu Thr Lys Glu Glu Ile Ala
130                 135                 140

Ala Thr Ala Ser Ile Ser Ala Ala Asp Thr Gln Ile Gly Ala Leu Ile
145                 150                 155                 160

Ala Glu Ala Leu Asp Lys Val Gly Lys Glu Gly Val Ile Thr Val Glu
                 165                 170                 175

Glu Ser Asn Thr Phe Gly Leu Glu Leu Glu Leu Thr Glu Gly Met Arg
             180                 185                 190

Phe Asp Lys Gly Tyr Ile Ser Gln Tyr Phe Val Thr Asp Ala Glu Arg
         195                 200                 205
```

```
Gln Glu Thr Val Leu Glu Asp Pro Tyr Ile Leu Ile Val Asn Ser Lys
    210                 215                 220

Ile Ser Asn Val Lys Asp Met Val Ala Ile Leu Glu Lys Val Met Gln
225                 230                 235                 240

Ser Gly Lys Pro Leu Leu Ile Ile Ala Glu Asp Val Glu Ala Glu Ala
                245                 250                 255

Leu Ala Thr Leu Ile Val Asn Lys Ile Arg Gly Leu Phe Lys Ser Val
            260                 265                 270

Ala Val Lys Ala Pro Gly Phe Gly Asp Arg Arg Lys Ala Gln Leu Ala
        275                 280                 285

Asp Ile Ala Ile Leu Thr Gly Gly Gln Val Ile Ser Glu Glu Val Gly
    290                 295                 300

Leu Ser Leu Glu Asn Ala Thr Leu Asp Leu Leu Gly Gln Ala Arg Lys
305                 310                 315                 320

Val Val Val Thr Lys Asp Glu Thr Thr Ile Val Glu Gly Ala Gly Asp
                325                 330                 335

Ala Glu Gln Ile Ala Gly Arg Val Ala Gln Ile Arg Ala Glu Ile Asp
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Pro Gly Gly Gly Val Ala
                405                 410                 415

Leu Ile Gln Ala Gly Val Lys Ala Phe Glu Thr Leu Asp Leu Glu Gly
            420                 425                 430

Asp Glu Ala Thr Gly Ala Asn Ile Val Arg Val Ala Ile Asp Ala Pro
        435                 440                 445

Leu Lys Gln Ile Ala Ile Asn Ala Gly Leu Glu Pro Gly Val Val Val
    450                 455                 460

Asp Lys Val Arg Gly Leu Pro Val Gly His Gly Leu Asn Ala Ala Thr
465                 470                 475                 480

Gly Val Tyr Glu Asp Leu Leu Pro Ala Gly Val Asn Asp Pro Val Lys
                485                 490                 495

Val Thr Arg Ser Ala Leu Gln Asn Ala Ala Ser Ile Ala Gly Leu Phe
            500                 505                 510

Leu Thr Thr Glu Val Val Val Ala Asp Lys Pro Gln Lys Asn Val Pro
        515                 520                 525

Ala Ala Pro Gly Gly Asp Glu Met Gly Gly Met Asp Asn
    530                 535                 540

<210> SEQ ID NO 3
<211> LENGTH: 9
<212> TYPE: PRT
<213> ORGANISM: Arthrobacter spp.

<400> SEQUENCE: 3

Lys Leu Ala Gly Gly Val Ala Val Ile
 1               5

<210> SEQ ID NO 4
<211> LENGTH: 16
<212> TYPE: DNA
```

```
<213> ORGANISM: Artificial Sequence
<220> FEATURE:
<223> OTHER INFORMATION: Primer

<400> SEQUENCE: 4
gtccgtcgcg ggcact                                                   16

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
cccacgatca ccaacga                                                  17

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
cctcgatgcg gtgcttg                                                  17

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
ccttgtccat sgcctcg                                                  17
```

HSP60 FROM ARTHROBACTER

CROSS REFERENCE TO RELATED APPLICATIONS

This application is a division of U.S. Ser. No. 10/543,366, filed on Jul. 26, 2005 now U.S. Pat. No. 7,297,783, issued Nov. 20, 2007, the disclosure of which is fully incorporated herein by reference, which is a national phase application of International Application No. PCT/EP/04/01368 filed on Feb. 13, 2004, claiming benefit of Great Britain Application No. 0303507.8, filed Feb. 14, 2003, each of which is herein incorporated by reference in its entirety.

FIELD OF THE INVENTION

The present invention relates to heat shock protein (hsp) genes and encoded proteins from Corynebacteria. In particular, it concerns the isolated DNA sequence and amino acid sequence of hsp60 from the genus *Arthrobacter*, and related sequences. Further, the invention relates to uses of *Arthrobacter* hsp60 in the preparation of vaccines, especially vaccines for fish, as an adjuvant, and as a carrier for antigens.

BACKGROUND OF THE INVENTION

A successful vaccine against intracellular pathogens will not only stimulate the humoral immune response via the Major Histocompatibility Complex (MHC) class II pathway, but (more importantly) will also induce destruction of infected cells through activation of the MHC class I pathway. The latter response is achieved through cytosolic degradation of foreign protein in infected cells, such that fragments of the foreign material are shuttled to the cell surface for presentation to $CD8^+$ cytotoxic T cells (CTL). Failure to activate the MHC class I pathway is a common deficiency of vaccines based on purified recombinant antigens.

Heat shock proteins ("Hsps") are a family of molecular chaperone proteins produced by prokaryotic and eukaryotic cells, and which play essential roles in a multitude of intra- and intercellular processes, in particular in antigen processing and presentation of antigen fragments to the MHC I system at the cell surface.

A live, non-virulent strain of *Arthrobacter* (a member of the family of Corynebacteria) is marketed under the name RENOGEN in a vaccine intended to protect salmon and other farmed fish against bacterial kidney disease (BKD). The characteristics of this strain are disclosed in WO 98/33884. This vaccine is unique in that it is the first live culture to have been licensed for use in aquaculture.

Surprisingly, it has now been shown that *Arthrobacter* hsp60 can be effectively employed in vaccines for fish against varied pathogens.

SUMMARY OF THE INVENTION

In a first aspect, the invention provides an isolated nucleic acid sequence comprising the sequence of the *Arthrobacter* hsp60 gene, a fragment thereof, or a homologous sequence. The gene includes the ORF, 5'UTR and 3'UTR, and any component promoter, enhancer, regulatory, terminator and localization elements.

In a second aspect the invention provides an isolated amino acid sequence comprising the sequence of *Arthrobacter* hsp60 protein, an immunogenic fragment thereof, or a homologous sequence, or a derivative.

In another aspect, the invention provides a vaccine composition comprising a nucleic acid sequence encoding an *Arthrobacter* hsp60 protein or comprising an *Arthrobacter* hsp60 polypeptide molecule, or an *Arthrobacter* cell extract enriched in hsp60. The vaccine composition can be used in the preparation of a medicament for human or veterinary use, including use in aquaculture.

In a further aspect the invention provides a kit comprising a vaccine composition according to the invention and a heterologous antigen or a nucleic acid sequence encoding a heterologous antigen, for separate, sequential or simultaneous administration.

In a further aspect of the invention there is provided a nucleic acid sequence encoding a fusion protein of whole or part of the hsp60 protein of *Arthrobacter* with a heterologous polypeptide. Also provided is the fusion protein itself.

The invention also provides DNA expression vectors carrying *Arthrobacter* hsp60 sequences, including chimeric sequences, and a host cell transformed with such a DNA expression vector.

In yet another aspect of the invention there is provided an entity comprising a polypeptide comprising whole or part of the hsp60 protein of *Arthrobacter*, which is covalently or non-covalently attached to a heterologous molecule.

In a further aspect of the invention there is provided use of *Arthrobacter* hsp60 protein or nucleic acid sequence as a vaccine antigen, as an adjuvant, or as a carrier for heterologous molecules, with the aim of treating or preventing animal diseases. Antibodies raised against *Arthrobacter* hsp60 and their medical uses are also provided.

In a further aspect there is provided a method of inducing or enhancing an immune response to an immunogen or a hapten in an animal, the method comprising administering to said animal a pharmaceutical composition comprising a hsp60 amino acid sequence according to the invention which is covalently or non-covalently linked to a heterologous molecule, wherein the heterologous molecule comprises said immunogen or hapten.

In another aspect the invention provides a method of therapeutic or prophylactic treatment of infectious disease in a fish, comprising administering to said fish a treatment composition comprising a hsp60 nucleic acid sequence or amino acid sequence according to the invention.

In another aspect of the invention there is provided use of the *Arthrobacter* hsp60 promoter to drive expression of a heterologous gene, in vitro or in vivo.

DESCRIPTION OF THE SEQUENCE LISTINGS

SEQ ID NO:1 is the coding DNA sequence (5' to 3') of the hsp60 gene isolated from *Arthrobacter* ATCC 55921 (nt. 953-2578), together with a portion of the 5' UTR sequence (nt. 1-952).

SEQ ID NO:2 is the amino acid sequence predicted from the ORF of the hsp60 gene sequence of SEQ ID NO:1.

SEQ ID NO:3 is the amino acid sequence of one hsp60 immunogenic fragment.

SEQ ID NOS:4-7 are nucleotide sequences of primers for amplification of *Arthrobacter* DNA in a PCR reaction.

DETAILED DESCRIPTION OF THE INVENTION

The novel sequences of the hsp60 gene of the invention and the encoded isolated or purified protein are provided as SEQ ID NO:1 and SEQ ID NO:2, respectively. To our surprise, we discovered that *Arthrobacter* hsp60 shares a CTL stimulating epitope with *Mycobacteria*, a specific nonapeptide (Mhsp65

(369-377)). The sequence of this epitope is KLAGGVAVI (SEQ ID NO:3. This strongly suggests that *Arthrobacter* hsp60 can activate the MHC I class pathway, and is therefore a very promising immune stimulating agent.

The invention encompasses nucleic acid sequences and amino acid sequences which are substantially homologous SEQ ID NO:1 and SEQ ID NO:2. "Substantially homologous" means that a sequence, when compared to a reference sequence, has at least 60% homology, preferably at least 70% homology, more preferably at least 75%, 80%, 85%, 90%, 95%, 98% or greater homology to the reference sequence.

To determine the percent homology of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence and the intervening non-homologous sequence in the gap can be disregarded for comparison purposes). There is no requirement for the two sequences to be the same length. In general, the length of sequence across which the sequences are compared is the entire extent of the alignment. Optionally, the length of a reference sequence aligned for comparison purpose is at least 30%, preferably at least 40%, more preferably at least 50%, even more preferably at least 60%, and even more preferably at least, 70%, 80%, or 90% of the length of the reference sequence. It possible to restrict homology analysis to any particular portion of the reference sequence.

When a position in the first (reference) sequence is occupied by the same amino acid residue or nucleotide as the corresponding position in the sequence, the molecules are homologous at that position (i.e. there is identity at that position). In the case of nucleic acid sequence comparison there is also homology at a certain position where the codon triplet including the nucleotide encodes the same amino acid in both molecules being compared, due to degeneracy of the genetic code.

The percent homology between two sequences is a function of the number of homologous positions shared by the sequences (i.e., % homology=no. of homologous positions/total no. of positions). Optionally, the comparison of sequences and determination of percent homology can be accomplished using a mathematical algorithm. Suitable algorithms are incorporated in to the NBLAST and XBLAST programs of Altschul et al. (1990) J. Mol. Biol. 215:430-10.

Also comprised within the nucleic acid sequences of the invention are homologous nucleic acid sequences which hybridize to the reference SEQ ID NO:1 under stringent conditions. "Stringent" hybridization conditions in the sense of the present invention are defined as those described by Sambrook et al., Molecular Cloning, A Laboratory Manual, Cold Spring Harbor Laboratory Press (1989), 1.101-1.104, i.e. a positive hybridization signal is still observed after washing for 1 hour with 1×SSC buffer and 0.1% SDS at 55° C., preferably at 62° C. and most preferably at 68° C., in particular for 1 hour in 0.2×SSC buffer and 0.1% SDS at 55° C., preferably at 62° C. and most preferably at 68° C.

The sequences of the invention include fragments of the reference nucleic acid sequence or amino acid sequence. A "fragment" of the hsp60 nucleic acid reference sequence is any part of that sequence comprising at least 50, optionally at least 75, or at least 100 consecutive nucleotides. One class of nucleic acid fragments has a maximum length of 600, preferably at most 300 nucleotides, more preferably at most 150 nucleotides. In one embodiment nucleic acid sequence fragments according to the invention comprise the ORF of SEQ ID NO:1. In another embodiment nucleic acid sequence fragments according to the invention encode an immunogenic protein fragment of hsp60.

A "fragment" of a hsp60 protein means any peptide molecule having at least 5, 10, 15, or optionally at least 25, 35, or 45 contiguous amino acids of the reference hsp60 amino acid sequence. One class of amino acid fragments has a maximum length of 200 amino acids, preferably at most 100 amino acids, more preferably at most 50 amino acids. An "immunogenic" protein fragment is one capable of eliciting antibodies that neutralize pathogen infectivity and/or mediate antibody-complement or antibody dependent cell cytotoxicity to provide protection of an immunized host. A preferred hsp60 immunogenic fragments is one incorporating the nonapeptide epitope of amino acid sequence KLAGGVAVI (SEQ ID NO: 3).

The amino acid sequences of the invention also comprise derivatives of the amino acid sequence of SEQ ID NO:2, or of homologues of that sequence. A "derivative" of an amino acid sequence is a sequence related to the reference sequence either on the amino acid sequence level (e.g. a homologous sequence wherein certain naturally-occurring amino acids are replaced with synthetic amino acid substitutes) or at the 3D level, i.e. molecules having approximately the same shape and conformation as the reference amino acid sequence. Thus, derivatives include mutants, mimetics, mimotopes, analogues, monomeric forms and functional equivalents. Amino acid sequence derivatives retain the ability to induce the production of antibodies that recognize and (cross)-react with the antigens from fish pathogens such as *R. salmoninarum* and/or to induce an immune response in fish that protects against infection with these pathogens.

Derivatives include, in particular, analogous molecules incorporating conservative amino acid substitutions, deletions, insertions, inversions or additions, which do not alter the immunological properties of the molecule. Conservative amino acid replacements include Ser/Ala, Ser/Gly, Asp/Gly, Asp/Asn, Ile/Val.

The hsp60 nucleic acid sequences of the invention may incorporate the Open Reading Frame (ORF) of the hsp60 gene, and may also incorporate the 5' Untranslated Region (UTR), or any portion thereof. The invention includes any component promoter, enhancer, regulatory, terminator and localization elements of SEQ ID NO:1, and use of these elements in conjunction with heterologous genes. In particular, the invention extends to a DNA expression vector comprising the promoter sequence of *Arthrobacter* hsp60 (from SEQ ID NO:1), or a substantially homologous sequence, linked to a heterologous gene, for driving expression of that gene.

The *Arthrobacter* hsp60 sequence listing provided herewith (SEQ ID NO:1) is the sequence of the gene identified by genomic cloning to be present in *Arthrobacter*, and SEQ ID NO:2 is the amino acid sequence inferred therefrom. A culture of the source *Arthrobacter* strain was deposited under Accession No. ATCC 55921 with the American Type Culture Collection (10801 University Boulevard, Manassas, Va. 20110-2209) on 20 Dec. 1996.

The hsp proteins of species of the same genus are generally very highly conserved, so it is to be expected that the sequences of hsp60 genes and proteins native to other Corynebacteria, and especially other *Arthrobacter* species, will not diverge greatly from SEQ ID NO:1 and SEQ ID NO:2, respectively. Therefore the present invention extends also to these related hsp60 molecules. Knowledge of sequence of the hsp60 gene from one Corynebacterial species facilitates isolation of the same genes from related organisms.

Procedures for isolation of these genes are well known in the art.

An "isolated" hsp60 gene or nucleic acid sequence is understood to mean the gene or sequence other than in its natural context within the *Arthrobacter* genome. DNA encoding hsp60 may be obtained from a cDNA library prepared from cell matter expressing the hsp60 (hsps are ubiquitous and expressed in abundance). The hsp60 encoding gene may also be obtained from a genomic library, such as by following steps described in Example 1, or by oligonucleotide synthesis.

Native hsp60 proteins can be isolated from bacterial cell sources by an appropriate purification scheme using standard protein purification techniques. The identity of the protein can be confirmed, for instance, by Western blotting or immunoprecipitation using antibodies to *Arthrobacter* ATCC 55921 hsp60 antigen. N-terminal amino acid sequencing can be used to determine partial or complete amino acid sequences. This enables design of probes to facilitate isolation of the native hsp60 sequence from a cDNA or genomic library.

Libraries can be screened with probes (such as antibodies to the hsp60 or oligonucleotides of at least about 20-80 bases) designed to identify the gene of interest or the protein encoded by it. For instance, the probes may be designed to be homologous to parts of the *Arthrobacter* gene sequence disclosed herein. Alternatively, the probes may have a high degree of homology with other bacterial hsp genes, such as the *Vibrio* hsp60 gene sequence. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding hsp60 is to use PCR methodology (Sambrook et al., supra; Dieffenbach et al., PCR Primer: A Laboratory Manual (Cold Spring Harbor Laboratory Press, 1995)).

Sequences identified in such library screening methods can be compared and aligned to the hsp60 disclosed in SEQ ID NO:1 or other known hsp sequences deposited and available in public databases such as GenBank. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

*Arthrobacter* hsp60 can be used as an adjuvant in pure or isolated form in conjunction with an antigen. An "adjuvant" as defined herein is a substance that nonspecifically augments the specific immune response to an antigen when mixed with the antigen prior to administration, or when administered separately into the same site. In one aspect of the invention isolated or purified *Arthrobacter* hsp60 protein is used as an adjuvant for an animal vaccine, especially a vaccine for fish. In a related application, the hsp60 gene or a portion thereof is provided on a DNA vector in order to adjuvant a nucleic acid vaccine. Within the scope of the invention there are provided vaccine compositions comprising the amino acid or nucleic acid sequences of the invention in conjunction with at least one other antigen or antigen-encoding nucleic acid sequence, and one or more pharmaceutically acceptable excipients. The other antigen may be a recombinant or isolated single antigen, or it may be a mixture of antigen molecules from a pathogen.

The use of *Arthrobacter* hsp60 as an adjuvant allows doctors and veterinarians to move away from use of the traditional attenuated live Mycobacterial adjuvants, which present a risk to the health of animals due to the danger of reversion to the virulent bacterial strain. There is an additional benefit for aquaculture in that injection of *Arthrobacter* hsp60 nucleic acid or isolated protein into fish does not result in disfiguring swellings or nodules at the injection site, which are common with conventional adjuvants and which lower the commercial value of the fish.

*Arthrobacter* hsp60 protein is not only effective in adjuvanting vaccines comprising other antigens, but it also has immunogenic activity in its own right. *Arthrobacter* hsp60 can provide the active principle for a vaccine to prevent or treat a variety of human and veterinary diseases, including diseases caused by fish pathogens, in particular, but not limited to, SRS and BKD. In a further aspect of the invention a vaccine composition comprises isolated or purified hsp60 protein as the sole antigenic or immunogenic component, together with one or more pharmaceutically acceptable excipients. Also provided is a nucleic acid vaccine composition comprising an expression vector comprising a hsp60 nucleic acid sequence of the present invention encoding an antigen being the sole antigenic or immunogenic component of the vaccine composition, together with one or more pharmaceutically acceptable excipients.

The highly immunogenic potential of *Arthrobacter* hsp60 suggests the possibility of preparing gene or peptide covalent conjugates (e.g. chimeras or fusions) of a hsp60 protein with a heterologous (non-hsp60) molecule, usually, but not limited to, a non-hsp protein (e.g. a hapten). In this manner, the *Arthrobacter* hsp60 protein acts as an adjuvant-free carrier to stimulate the humoral and cellular immune responses to the accompanying heterologous molecule. As used herein the term "carrier" refers to a molecule containing T cell epitopes which, when covalently linked to a second molecule, helps to elicit and enhance immune responses to the second molecule (which may be a protein, peptide, oligonucleotide or oligosaccharide).

This approach to vaccine development is particularly advantageous when the antigenic peptide concerned is not very large and poorly immunogenic, yet would be a suitable target for a vaccine. The heterologous molecule carried by the *Arthrobacter* hsp60 is advantageously a protein hapten or a non-protein molecule such as a carbohydrate moiety.

As used herein, a hsp60 "fusion protein" comprises a hsp60 polypeptide operatively linked to a different polypeptide (a "heterologous polypeptide"). A "heterologous peptide" or a "non-hsp60 polypeptide" refers to a polypeptide having an amino acid sequence corresponding to a protein which is not substantially homologous to a hsp60 protein. Within a hsp60 fusion protein the hsp60 polypeptide can correspond to all or a portion of a hsp60 protein. Within the fusion protein, the term "operatively linked" indicates that the hsp60 polypeptide and the non-hsp60 polypeptide are fused in-frame to each other. The non-hsp60 polypeptide can be fused to the N-terminus or C-terminus of the hsp60 polypeptide, or can be embedded within the hsp60 polypeptide.

It is possible to link a hsp60 polypeptide and a heterologous molecule by means of a covalent or non-covalent linkage other than by creating a fusion protein. A "heterologous molecule" is any protein, peptide, oligonucleotide or oligosaccharide molecule other than a hsp60 protein. For instance, chemical spacer groups may be inserted between polypeptides, e.g. to create a molecule of general formula hsp60-X-heterologous polypeptide, where X is a spacer group, such as a short sequence of one or more amino acids. Alternatively, the hsp60 polypeptide may be covalently linked other than through amide linkages in a linear chain of amino acids, for instance by chemical conjugation or by chemical, light (e.g. UV)—or radiation-induced crosslinking to the non-hsp molecule. Glutaraldehyde and mercapto-binding linkers are examples of suitable chemical cross-linkers. Specific possibilities are EDC+NHS or sulfo-NHS, sulfo-SMCC, sulfo-SBED, and SAED, which are commercially available in kit form.

In a preferred embodiment of the invention, the hsp60 polypeptide is conjugated to a hapten. A hapten is a substance of low molecular mass (e.g. a peptide or oligosaccharide) that can bind antibodies, but which will induce an immune response only if covalently attached to a large carrier molecule.

It is possible to conjugate hsp60 with entire populations of proteins from antigenic cells or particles by in vitro complexing of cell lysates, fractions, extracts, viral particles, and the like.

The heterologous molecules or polypeptides can be from any source, but are most likely to be components of a pathogenic organism. In particular they may be polypeptides from viral, bacterial, protozoan, helmintic, or fungal pathogens of animals, especially aquatic animals.

The isolated hsp60 gene from *Arthrobacter* can be exploited in the conventional manner, by cloning the gene into an expression vector for generation of large quantities of purified or isolated recombinant hsp60 protein (or hsp60 fusion protein). A purified hsp60 antigen can also be obtained by non-recombinant techniques. The protein is abundant and can be extracted from cells by conventional purification methods. Alternatively, the hsp60 protein or polypeptide can be synthesized chemically using standard peptide synthesis techniques. A vaccine comprising this purified or isolated recombinant or non-recombinant protein can be termed an antigen-based vaccine.

An "isolated" or "purified" protein is defined as being substantially free of cellular material or other contaminating proteins from the cell or tissue source from which the hsp60 protein is derived, or substantially free from chemical precursors or other chemicals when chemically synthesized. The language "substantially free of cellular material" includes preparations of hsp60 protein in which the protein is separated from cellular components of the cells from which it is isolated or recombinantly produced. In one embodiment, the language "substantially free of cellular material" includes preparations of hsp60 protein having less than about 30% (by dry weight) of non-hsp60 protein (also referred to herein as a "contaminating protein"), more preferably less than about 20% of contaminating protein, still more preferably less than about 10% of contaminating protein, and most preferably less than about 5% contaminating protein. When the hsp60 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

A hsp60 "enriched" *Arthrobacter* cell extract may also be used in performance of the invention as an alternative to isolated or purified hsp60. An "enriched" cell extract can be obtained by inactivating or killing whole *Arthrobacter* cells, lysing the cells, fractionating the resulting cell lysate by conventional means, and identifying fractions in which hsp60 protein is more abundant compared with other fractions (for instance by Western blotting). A hsp60 enriched cell extract can also be prepared by cultivating *Arthrobacter* cells under conditions which result in elevated expression of heat shock proteins (i.e. under heat or other cellular stress conditions), and inactivating or killing, and lysing the cells. Optionally the resulting cell extract (lysate) is fractionated and hsp60-rich fractions are identified.

Preferably, a hsp60 chimeric or fusion protein of the invention is produced by standard recombinant DNA techniques. For example, DNA fragments coding for the different polypeptide sequences are ligated together in-frame in accordance with conventional techniques, for example by employing blunt-ended or staggered-end termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, eds. Ausubel et al. John Wiley & Sons: 1992).

Another aspect of the invention pertains to vectors, preferably expression vectors, comprising a nucleic acid sequencing encoding hsp60 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of directing the expression of genes to which they are operatively linked. Such vectors are referred to herein as "expression vectors". In general, expression vectors of utility in recombinant DNA techniques are in the form of plasmids. However, the invention is intended to include other forms of expression vectors, such as viral vectors (e.g., replication defective retroviruses, adenoviruses and adeno-associated viruses), which serve equivalent functions.

The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, operatively linked to the nucleic acid sequence to be expressed. Expression vectors of the invention may be used for expression within the intended recipient of the hsp60 antigen (as a DNA vaccine) or for expression within a host organism other than the final recipient (for production of recombinant antigen vaccines).

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g. hsp60 proteins, mutant forms of hsp60, fusion proteins of hsp60 with a heterologous peptide, etc.).

Another aspect of the invention pertains to host cells into which a recombinant expression vector of the invention has been introduced. A host cell can be any prokaryotic or eukaryotic cell (including a eukaryotic cell within a multicellular eukaryotic organism). For example, hsp proteins can be expressed in bacterial cells such as *E. coli*, insect cells (using baculovirus expression vectors), yeast cells or mammalian cells. Other suitable host cells are known to those skilled in the art (e.g. Goeddel, supra). The recombinant expression vector may be designed to be expressed in a host fish cell (following DNA vaccination). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose binding protein, or protein A, respectively, to the target recombinant protein.

The hsp60 gene can be incorporated into a Nucleic Acid Vaccine (NAV), whereby the NAV is taken up by host cells of a living animal, and expression of the hsp60 gene takes place within the cytosol. Because short peptides of intracellular hsp60 antigens are transported to the cell surface where they can make contact with the MHC I system, NAV-originating hsp60 antigens are ideally positioned for inducing a cellular immune response.

A hsp60 gene inserted into a DNA vector can be inoculated directly into a fish (e.g. orally, intramuscularly or intraperitoneally) for expression in vivo within fish cells. DNA vaccination can also be carried out in other animal species. Thus, in one aspect of the invention there is provided a nucleic acid vaccine comprising a pharmaceutically acceptable carrier and a DNA plasmid on which a nucleic acid sequence encoding *Arthrobacter* hsp60 is operably linked to a transcriptional regulatory sequence. Transcriptional regulatory sequences include promoters, polyadenylation sequences and other nucleotide sequences such as the immune-stimulating oligonucleotides having unmethylated CpG dinucleotides, or nucleotide sequences that code for other antigenic proteins or adjuvanting cytokines. The presence of eukaryotic or viral transcriptional regulatory sequence(s) allows expression of the hsp60 gene in fish cells. The DNA plasmid itself can be replicated in bacterial cells in order to prepare a vaccine composition, but generally lacks transcriptional regulatory sequences permitting hsp60 gene expression within prokaryotic cells. For optimal in vivo expression it may be preferred to select transcriptional regulatory sequences endogenous to the fish to be vaccinated. For instance, endogenous cytokine or actin gene promoters may be considered. The DNA can be present in naked form or it can be administered together with an agent facilitating cellular uptake (e.g. liposomes or cationic lipids).

The technology of DNA vaccination of fish is explained in more detail in U.S. Pat. No. 5,780,448, which is incorporated herein by reference.

The present invention also relates to a method of generating monoclonal or polyclonal antibodies to a molecule using a conjugate of a hsp60 protein joined to the molecule. In this embodiment, an effective amount of the conjugate (i.e., an amount which results in an immune response in the host) is introduced into an animal host which results in production of antibodies to the substance in the host. The antibodies are removed from the host and purified using known techniques (e.g. chromatography), thereby resulting in production of polyclonal antibodies. Alternatively, the antibodies produced using the method of the present invention can be used to generate hybridoma cells which produce monoclonal antibodies using known techniques.

In one embodiment of the invention the promoter sequence of the *Arthrobacter* hsp60 gene is used to drive expression of a heterologous gene, i.e. a gene other than the gene encoding *Arthrobacter* hsp60. The promoter can be inserted upstream of a heterologous gene in the chromosomal DNA of an organism, or into an extrachromosomal plasmid or other expression vector. For instance, in the event that it is desired to overexpress an endogenous *Arthrobacter* gene, or to insert a foreign gene into an endogenous plasmid of *Arthrobacter*, an upstream hsp60 promoter can drive expression of that heterologous gene in response to a stimulus such as heat shock.

The vaccines manufactured in accordance with the methodology of the invention are suited for administering to any species of animal having a humoral and/or cellular immune system comparable to that of mammals. Human beings are included within the meaning of "animal" and "mammal" in the present context. *Arthrobacter* hsp60 can be employed to adjuvant any vaccine for mammals, birds, reptiles or fish. Similarly, *Arthrobacter* hsp60 can be used in vaccines as carriers for covalently-attached antigens, optionally to the exclusion of any conventional adjuvant (so-called "non-adjuvant" vaccines). *Arthrobacter* hsp60 is also capable of being used as an immunogen (optionally as the sole immunogen) in a vaccine for raising an immune response against specific diseases, notably Salmonid Rickettsial Septicemia (SRS), Bacterial Kidney Disease (BKD) and other infectious diseases in fish.

The term "vaccine" is used in the broad sense, and includes not only compositions to be used for immunization against pathogens, but also anti-tumor vaccines, vaccines based on autogenous antigens (e.g. for chemical castration), and so on. Within the sphere of veterinary vaccination, the major species of land animals to be considered for immunization include cattle, horses, sheep, swine and poultry birds. For aquaculture, the vaccines of the invention can be employed in shellfish or finfish, especially for treatment of teleosts such as salmon, trout, carp, sea bream, sea bass, yellowtail, catfish, halibut, haddock, or optionally for treatment of other aquatic species such as crustaceans (e.g. shrimps, prawns, lobster, carbs) and mollusks (e.g. oysters, mussels). There are no limits to the candidate antigens suitable for combining with *Arthrobacter* hsp60 sequences in a vaccine. Pathogenic antigens can be derived from bacteria, viruses, protozoa, nematodes and fungi. One particular focus is on antigens, particularly surface antigens, of fish pathogenic organisms.

Hsp60 amino acid or nucleic acid sequences can be used in vaccine compositions in conjunction with, or conjugated to, bacterial, protozoan, viral or fungal antigens from diseases affecting shellfish or finfish, including antigens (or their coding sequences) derived from: Infectious Salmon Anaemia Virus (ISAV), Infectious Pancreatic Necrosis Virus (IPNV), Infectious Hematopoietic Necrosis Virus (IHNV), Iridovirus, Nervous Necrosis Virus (NNV), Salmon Pancreas Disease Virus (SPDV), Spring Viremia of Carp Virus (SVCV), Viral Hemorrhagic Septicemia Virus (VHSV), Yellow-head virus (YHV), Taura Syndrome Virus (TSV), White Spot Syndrome Virus (WSSV), *Renibacterium salmoninarum* (causative agent of Bacterial Kidney Disease), *Piscirickettsia salmonis* (causative agent of Salmonid Rickettsial Septicemia), *Vibrio* spp, *Aeromonas* spp, *Yersinia ruckerii, Pseudomonas* spp, *Photobacterium damselae*, etc. A large and growing number of polypeptides from these and other pathogenic organisms have been purified and/or cloned and expressed and are available to be conjugated to, or provided in conjunction with, *Arthrobacter* hsp60 or its coding sequence in a vaccine composition. Preferred examples include IPNV proteins VP1, VP2, VP3 and NS and their coding nucleotide sequences; ISAV proteins disclosed in WO 01/10469 including hemagglutinin, nucleocapsid, polymerase and segment 7 P4 and P5 proteins, and their coding nucleotide sequences; *P. salmonis* proteins disclosed in WO 01/68865 including OspA and IcmE and their coding nucleotide sequences; nodavirus proteins such as the nucleocapsid; and structural polypeptides from SPDV and their coding nucleotide sequences (disclosed in WO 99/58639). A preferred vaccine composition according to the invention comprises a DNA expression vector carrying the hsp60 nucleotide sequence fused in-frame with the IPNV VP2 sequence or the IPNV VP3 sequence. Optionally, the vaccine comprises a first plasmid carrying the hsp60-VP2 fusion and a second plasmid carrying the hsp60-VP3 fusion.

Hsp60 sequences can also be used in conjunction with, or conjugated to, antigens (or their coding sequences) from other animal pathogens and parasites, including: Bovine Viral Diarrhea Virus (BVDV), Bovine Herpes virus (BHV), Foot and mouth disease virus, Bovine Respiratory Syncytial Virus (BRSV), Parainfluenza type 3 virus (PI3), Infectious Bovine Rhinotracheitis (IBR), Porcine Respiratory and Reproductive Syndrome Virus (PRRSV), *Mycobacteria, Leishmania, Ehrlichia, Eimeria, Clostridia, Pasteurella, Mycoplasma* (e.g. *M. bovis, M. hyopneumoniae*) *Leptospira, Brachyspira, Salmonella, Brucella, Neospora, Cryptosporidium, Fusobacterium, E. coli, Rotavirus, Coronavirus, Mannheimia haemolytica, Haemophilus somnus, Actinobacillus pleuropneumoniae, Trypanosoma, Anaplasma, Treponema*, etc.

The invention encompasses the use of hsp60 sequences in conjunction with any of the above-mentioned antigens or their coding sequences in the manufacture of a pharmaceutical composition for the treatment or prevention of disease caused by infection with the disease agent from which the antigen is derived.

In one embodiment of the invention, *Arthrobacter* hsp60 protein or nucleic acid sequence is included in a vaccine further comprising *Arthrobacter* hsp70 protein or nucleic acid sequence. The combination of these two genes or antigens in a single vaccine composition can lead to additive or synergistic improvements in vaccine efficacy. *Arthrobacter* hsp70 is the subject of co-pending application PCT/EP03/07602, filed 14 Jul. 2003.

The vaccine antigens provided in conjunction with hsp60 gene or protein may be chemically conjugated to the hsp60 (in a chimera or fusion protein) or they may be provided as separate molecules together in a single vaccine composition.

As another option, hsp60 gene or protein may be provided with an antigen or antigen-encoding nucleic acid sequence in a kit for separate, sequential or simultaneous administration. The vaccine antigens provided ion conjunction with hsp60 gene or protein can be bacterins, cell extracts, recombinant proteins, plasmid-borne genes, or live/attenuated pathogen strains.

It is possible to immunize a subject with the neutral or the salt forms of the present fusion proteins or isolated hsp60 protein, either administered alone or in admixture with a pharmaceutically acceptable vehicle or excipient. Typically, vaccines are prepared as liquid solutions or suspensions; solid forms (e.g. lyophilized matter) suitable for solution in, or suspension in, liquid vehicles prior to administration may also be prepared. The preparation may be emulsified or the active ingredient encapsulated in liposome vehicles. The pharmaceutical compositions of the invention may be administered in a form for immediate release or by extended release.

Pharmaceutically acceptable excipients or vehicles to be admixed with the antigen or nucleic acid molecule of the invention in preparing a vaccine composition are, for example, water, saline, dextrose, glycerol, auxiliary substances such as wetting or emulsifying agents, bulking agents, binders, disintegrants, diluents, lubricants, pH buffering agents, or adjuvants such as muramyl dipeptides, avridine, aluminium hydroxide, oils, saponins, block co-polymers and other substances known in the art.

To immunize a subject, a hsp60 antigen or hsp fusion protein or hsp60 gene vector can be administered parenterally, usually by intramuscular injection in an appropriate vehicle, but optionally by the subcutaneous route, by intravenous injection or by intradermal or intranasal delivery. In the case of antigen immunization of fish, the typical routes of administration are by injection into the peritoneal cavity, intra-muscular injection, orally in feed, or by immersion. The preferred antigenc vaccine compositions of the invention are in a form suitable for administration by injection or immersion. DNA vaccination is generally by intra-muscular injection.

The effective dosage may vary depending on the size and species of the subject, and according to the mode of administration. The optimal dosage can be determined through trial and error by a doctor or veterinarian. Typically, a single dose of hsp60 antigen will be in the range of from about 0.01 to 1000 µg per kg body weight, preferably 0.5 to 500 µg per kg, more preferably 0.1 to 100 µg per kg. For DNA vaccines, a minimum dosage of 10 pg up to dosages of 1000 µg of plasmid per animal will allow for expression of the antigen in vivo.

The novel antigens disclosed as part of the present invention are also useful in screening for antibodies to pathogenic proteins, and in screening for toxic and environmental stresses/stress effects. The invention additionally includes diagnostic uses of these antigens, for instance in the preparation of a diagnostic kit, useful for testing animals for the presence of disease-causing organisms.

Antibodies raised against purified hsp60 antigen and/or hsp60 fusion proteins as disclosed herein are also comprised within the invention. It is contemplated such antibodies could have both diagnostic and therapeutic applications in disease management and fish health. Both polyclonal antibodies and monoclonal antibodies may be useful in this respect. Procedures for immunizing animals, eg. mice, with proteins and selection of hybridomas producing immunogen-specific monoclonal antibodies are well know in the art (see for example Kohler and Milstein (1975) Nature 256: 495-497).

Sandwich assays and ELISA may be mentioned as specific examples of diagnostic assays.

The hsp60 nucleic acid sequence of the invention has diagnostics applications, for instance in the design of primers for PCR amplification assays.

EXAMPLES

Example 1

Isolation and Sequencing of Hsp60 Gene from the Genome of *Arthrobacter* ATCC 55921

A 5 ml culture of *Arthrobacter* ATCC 55921 is grown overnight shaking at 30° C. in LB containing kanamycin (30 µg/ml). DNA extraction is then carried out using the PURE-GENE DNA isolation kit (Gentra) or INSTAGENE Resin according to the manufacturer's instructions.

PCR Using Conserved Mycobacterial Sequences

Areas of greatest similarity between several mycobacterial and streptomyces hsp60 (groEL) sequences at the nucleotide level are used to design primers for PCR and sequencing of the *Arthrobacter* hsp60 gene. The selected primers include groEL-OFP (5'-GTCCGTCGCGGGCACT-3'), (SEQ ID NO: 4), groEL-IF (5'-CCCACGATCACCAACGA-3')(SEQ ID NO: 5), groEL-1R (5'-CCTCGATGCGGTGCTTG-3'), (SEQ ID NO: 6), groEL-2R, (5'-CCTTGTCCATSGCCTCg-3', (SEQ ID NO: 7). These primers are used for amplification of *Arthrobacter* DNA in a PCR reaction with a 50° C. or 60° C. annealing temperature and varying amounts of Magnesium and DMSO. DNA fragments of approximately 595 bp and 1050 bp are amplified using primers OFP/2R and 1F/1R respectively. The PCR products are cleaned using QIAGEN PCR clean up kit (according to the manufacturer's instructions) and sequenced according to the manufacturer's instructions using BIGDYE primer chemistry (Applied Biosystems) using each of the primers used for the PCR. Briefly, the extension reaction mixtures are prepared using the ABI PRISM (8 µl) BIGDYE Terminator Cycle Sequencing Ready Reaction mix, ~600 ng of DNA template, 3.2 pmol of the appropriate primer and ddH$_2$O to 20 µl. Conditions for cycle sequencing are as follows: the thermal cycler is set to 25 cycles consisting of 96° C. for 10 s, 50° C. for 5 s, and 60° C. for 4 min. The sequence shows this fragment to contain high homology to the groEL genes of several mycobacteria and it is used as a starting point for genome walking.

Genome Walking

Genome walking is used to extend the sequence 5' and 3' of the already identified sequences. Primers are designed from the hsp60-like sequences described above as described in the Genome Walker manual (Clontech). Initially, four genomic libraries are made (DraI, EcoRV, PvuII, StuI), and subsequently three additional libraries are made (AluI, ScaI, and SnaF1). All libraries and the subsequent PCR reactions are as described in the Genome Walker manual. Several rounds of Genome walking are performed to extend the gene sequence.

Sequences are aligned into contigs using Genecode's Sequencher software. A Genbank search using the contigged sequences confirms the contig contains the hsp60 gene.

The *Arthrobacter* hsp60 protein (and gene) can be seen to bear a resemblance to homologues in other genera, especially bacterial species.

Example 2

Nucleic Acid Vaccine Against IPNV Based on Gene Fusions with Hsp60

Atlantic salmon (*Salmo salar*) pre-smolts (35-40 g) maintained in flow through fresh water are anaesthetized with benzocaine diluted in clean aquarium water. Prior to vaccination 6 fish are euthanized by lethal overdose of anaesthetic and bled from the caudal vein for pre-immune serum.

The nucleic acid vaccines and PBS control are vaccinated intramuscularly into the left dorsal flank, just below the dorsal fin, with 50 µl of vaccine. Forty fish are vaccinated per replicate (80 per group, divided between two tanks). Following vaccination fish are allowed to recover in fresh water and allocated to their appropriate tank.

The nucleic acid vaccines undergoing testing are: pUKrsxHSP60-ipnVP2 and pUKrsxHSP60-ipnVP3. These plasmids carry, under the control of a CMV promoter, an in-frame fusion of the complete coding sequences of *Arthrobacter* hsp60 and IPNV VP2 or IPNV VP3, respectively. pUKrsxHSP60-ipnVP2 is tested alone, and both plasmids are also tested together.

For comparison, plasmids are also prepared comprising IPN VP2 protein fused 3' of a sequence known from previous studies to boost the immunoprotective efficacy of the VP2 component by about 20% (i.e. a "gold standard" VP2-based IPNV nucleic acid vaccine).

6 weeks post vaccination the fish are transferred to seawater. On the day prior to challenge serum is samples from 4 fish per replicate group. A sample of muscle from the injection site is also taken and formalin fixed to look for vaccine presence. On day 21 post challenge, serum is sampled from a maximum of 4 surviving fish per replicate group. Following challenge, mortalities are removed daily on first observation and kidneys samples and frozen for analysis by ELISA.

Challenge takes place 4-6 weeks after seawater transfer, by cohabitation with marked sibling fish which have been challenged by intraperitoneal injection of virulent IPNV ($10^6$ cfu). The trial is terminated after 20 weeks.

The results indicate that all of the nucleic acid vaccines based on the VP2 sequence of IPNV are protective against challenge by the virus, including the hsp60-VP2 fusion.

Example 3

Recombinant Hsp60 in a Vaccine Against ISAV

Atlantic salmon parr are acclimated to 0.5 m holding tanks supplied with aerated flowing well water (10° C.) for a week prior to the start of the experiment and fed daily throughout the entire experiment. Each group of 55 fish is split into 2 tanks of 25 to provide for replicate treatment groups. Atlantic salmon parr experience between 60 and 80% mortality when challenged with ISAV.

The fish are anaesthetized and then vaccinated by intraperitoneal injection with 0.2 ml saline, or 0.2 ml saline containing the specific recombinant proteins. The negative control is a PBS injection (saline). The treatment groups are: (A) His-tagged purified *Arthrobacter* hsp60 recombinant protein, 12 μg; (B) ISAV recombinant His-tagged nucleocapsid protein (NC), 12 μg; (C) His-tagged purified *Arthrobacter* hsp60 recombinant protein, 12 μg, admixture with His-tagged ISAV NC, 12 μg; (D) His-tagged purified *Arthrobacter* hsp60 recombinant protein, 12 μg, crosslinked to His-tagged ISAV NC, 12 μg.

Treatment group D receives covalently crosslinked proteins. EDC and sulfo-NHS are used as crosslinking agents, and employed according to standard protocols.

A cohabitation challenge is used, in which a small number of salmon are given an i.p. injection with 0.1 ml cultured virulent ISAV (~$10^4$ $TCID_{50}$ per fish) and added to each tank of treated fish. Mortalities in each tank are monitored daily.

The relative percentage survival is assessed by comparing mortalities between the different treatment groups and controls at specific time-points

We claim:

1. An isolated nucleic acid sequence encoding an *Arthrobacter* hsp60, wherein the isolated nucleic acid sequence is fused in-frame to a heterologous coding sequence, wherein the *Arthrobacter* hsp60 comprises the amino acid sequence shown as SEQ ID NO:2.

2. An isolated nucleic acid sequence encoding an *Arthrobacter* hsp60, wherein the isolated nucleic acid sequence is fused in-frame to a heterologous coding sequence, wherein the isolated nucleic acid sequence comprises nucleotides 953-2578 of SEQ ID NO:1.

* * * * *